United States Patent [19]

Nakada

[11] Patent Number: 5,312,839
[45] Date of Patent: May 17, 1994

[54] COMPOUNDS AND METHOD FOR PROTECTION OF CELLS AND TISSUES FROM IRREVERIBLE INJURY DUE TO LACTIC ACIDOSIS

[75] Inventor: Tsutomu Nakada, San Francisco, Calif.

[73] Assignee: Regents of the University of California, Oakland, Calif.

[21] Appl. No.: 664,933

[22] Filed: Mar. 5, 1991

[51] Int. Cl.$^5$ .................... A01N 37/52; C07C 239/00
[52] U.S. Cl. .................... 514/634; 514/665; 514/558; 514/238.8; 514/231.2; 562/104
[58] Field of Search ............ 514/558, 665, 634, 231.2, 514/238.8

[56] References Cited

U.S. PATENT DOCUMENTS 3,943,253 3/1976 Barer et al. .................... 514/558

OTHER PUBLICATIONS

Nakada, T. et al, "Intrauterine Fetal Brian NMR Spec . . . " *Magn. Reson. Med.,* 12(2), 172–80, 1989.
Yorifuji, et al, "Gratuitous Introduction of 2-ω-Guanidino Acid Amidinohydrolases" Aug. 27, 1981 Department of Agricultural and Biological Chemistry, pp. 317–318.
*A Comparison of Two Cerebral Perfusion Tracers, N-Isopropyl 1-123 p-Iodoamphetamine and 1-123 HIPDM, in the Human,* Clinical Sciences, Investigative Nuclear Medicine, vol. 25, No. 1, pp. 25–30, 1984.
*The Effect of Anaesthetics on the Uptake of Brian-imaging Agents in Rats,* Nuclear Medicine Communications 6, 75–81 (1985), pp. 75–81.
N-Isopropyl-[$^{123}$I]p-Iodoamphetamine: Single-Pass Brain Uptake and Washout; Binding to Brain Synaptosomes; and Localization in Dog and Monkey Brain, The Journal of Nuclear Medicine, vol. 21, No. 10, pp. 947–952, 1980.
*A New Brain Perfusion Imaging Agent:* [*I-123-*]*HIPDM:N,N,N,-Trimethyl-N$^1$-*[2-Hydroxy-3-Methyl-5-Iodobenzyl]-1,3 Propanediamine, The Journal of Nuclear Medicine, vol. 24, No. 1, pp. 66–72, 1983.
*Development of 1-123-Labeled Amines for Brian Studies: Localization of 1-123 Iodophenylalkyl Amines in Rat Brain,* Radiochemisty and Radiopharmaceuticals, The Journal of Nuclear Medicine, vol. 21, No. 10, pp. 940–945, 1980.
*Regional Intracellular pH Shift: A Proposed New Mechanism for Radiopharmaceuitcal Uptake in Brain and Other Tissues,* Preliminary Notes, The Journal of Nuclear Medicine, vol. 21, No. 2, pp. 147–152, 1980.
J. Rigandy, S. P. Klesney, *Nomenclature of Organic Chemistry,* IUPAC, p. 58, Pergamon Press, (1979).
N. Irving Sax, R. J. Lewis, *Hawley Condensed Chemical Dictionary,* p. 595, 11th Ed., Van Nostrand Reinhold Company, N.Y. (1987).
D. B. Guralnik, *Webster's New World Dictionary,* p. 920, 2nd College Ed., William Collins Publ., Inc., (1979).
T. Nakada, I. Kwee, S. Suzuki, and K. Houkin, Intrauterine Fetal Brain NMR Spectroscopy:$^1$H and $^{31}$P Studies in Rats *Magnetic Resonance in Medicine* 12: 172–180(1989).

*Primary Examiner*—Jose' G. Dees
*Assistant Examiner*—Keith MacMillan
*Attorney, Agent, or Firm*—Hana Dolezalova

[57] ABSTRACT

Compounds and a method useful for protection of tissue cells in a mammalian body from irreversible damages due to lactic acidosis caused by oxygen deficiency. The protection is achieved by administering a compound having a cell membrane permeability and/or ability to cross the blood brain barrier and being able to provide a buffering action to prevent an increase in a hydrogen ion concentration over the physiologically acceptable levels.

8 Claims, 4 Drawing Sheets

▨ Survived
☐ Dead

COMPOUNDS AND METHOD FOR PROTECTION OF CELLS AND TISSUES FROM IRREVERIBLE INJURY DUE TO LACTIC ACIDOSIS

The present invention was made in the course of research supported by the research grant GM 37197 from the National Institute of Health. The United States Government may have certain rights in this invention.

BACKGROUND OF INVENTION

Field of Invention

The present invention relates to compounds and to a method for protection of cells and tissues from irreversible injury due to lactic acidosis. More specifically, this invention relates to compounds permeable through the cell membrane and possessing a buffering action against an increase in hydrogen ion concentration and also to a method for protection of tissues and cells in mammals, including humans, from the irreversible damages due to lactic acidosis caused by the accumulation of lactic acid in the cells under the condition of oxygen deficiency such as anoxia, hypoxia or ischemia.

BACKGROUND ART AND RELATED ART DISCLOSURES

Cellular hypoxia or anoxia represents one of the fundamental sequelae of compromise in the microcirculation. In brain, which is heavily dependent on glucose as an energy source, cellular hypoxia or anoxia results not only in a reduction in energy production but also in lower pH, leading to the tissue acidosis. Anaerobic glycolysis generates two excess protons from one molecule of D-glucose according to the equation:

$$\text{D-Glucose} + 2\text{Pi} + 2\text{ADP}^{2-} \rightarrow 2\text{L-lactate} + 2\text{H}^- + 2\text{ATP}^{4-}$$

Recent findings show that in addition to maintenance of ATP above critical cellular levels, preservation of a normal pH in the presence of excess protons is of fundamental importance to cell survival.

Cells, particularly cells of the central nervous system, also called neuronal cells, neurons, or cerebral cells, are heavily dependent on glucose as an energy source. When neuronal cells are placed under the condition of oxygen deficiency such as anoxia, hypoxia or ischemia, the normal oxidative metabolism is inhibited and substituted with anaerobic glycolysis. The glycolytic pathway for production of glucose in the absence of oxygen is not only uneconomical but it also produces lactic acid. As the result of anaerobic glycolysis, lactic acid is accumulated in neuronal or other cells resulting in lactic acidosis. If the lactic acidosis is permitted to develop and persist for certain time in cells, those cells are irreversibly injured and damaged. This is known as the "Lactate Hypothesis" described for example in *Neurology*, 33: 229 (1983); *Stroke*, 11: 355 (1980); *J. Neurochem.*, 52: 154 (1989).

Lactic acidosis was shown to play a key role in determining the outcome of brain anoxia or ischemia. Conditions which permit higher glucose supplies to anoxic or ischemic brain tissue such as systemic hyperglycemia, complete anoxia, or partial ischemia, consistently result in higher levels of lactate, an unfavorable condition for cell survival (*Arch. Neurol.*, 34:65 (1977)). In contrast, conditions such as fasting, which limit lactate production, can prevent reactive hyperglycemia during anoxia or partial ischemia and provide a favorable outcome.

Since it appears that the acidosis is more harmful to brain than the lactate molecule per se, theoretically, conditions which permit higher acid buffering capacity should also protect brain against anoxic or ischemic insults. This invention concerns compounds having such capability.

For protection of the central nervous system and other cells in mammals from irreversible injury caused by oxygen deficiency, compounds such as calcium antagonists, e.g. flunarizine or dextromethophan, and free radical scavengers such as barbitals were previously used. Calcium antagonists are intended to prevent the influx of calcium ions into the neuronal cells due to exhaustion of energy, while free radical scavengers are used to prevent cell damage caused by active oxygen produced by the free radical capturing mechanism connected with glycolysis to provide energy. Thus, the currently used conventional drugs are directed only to treatment of the phenomena caused by the cessation of the energy supply in cerebral cells.

On the other hand, tromethamine having a chemical formula 2-amino-2-hydroxymethyl-1,3-propanedil is a known drug for treatment of acidosis. This drug reacts with carbonate ion present in blood circulation and in this way it enhances the bicarbonate ion concentration. It is not intended to neutralize hydrogen ion in cells directly. Sodium bicarbonate is similarly usable in cells to prevent acidosis by neutralizing hydrogen ion and to retain a normal bicarbonate ion concentration in blood. Thus, conventional drugs for acidosis treatment are all concerned with the control of a carbonate buffering system.

Since the excessive formation of hydrogen ion causes the change in intracellular pH, it would be highly advantageous to have available a drug or mechanism to maintain the normal intracellular physiological pH.

It has recently been discovered and described, for example, in *Neurology*, 40 (Supp. 1), 281 (1990), that immediately after birth the cerebral cells of newborn mammals are highly resistant to oxygen deficiency. For instance, newborn rats were shown to survive for up to 12 minutes even in such extreme conditions as when being placed under a pure nitrogen atmosphere.

These findings points out toward newborns possessing some additional mechanism by which they can counter the insufficient supply of oxygen and prevent the cells, primarily the central nervous system cells, from irreversible injury and damage caused by cellular hypoxia or anoxia. If such substance and/or system is present in newborns and such compound or the components of such system could be identified and utilized for the adults, it could effectively prevent and/or protect the development of irreversible change in the cells caused by metabolic acidosis, anoxia, hypoxia or ischemia. Such compounds and/or system would have to be non-toxic, physiologically acceptable, permeable through the cell membrane, be able to cross the blood-brain barrier and have a buffering action to neutralize the increase in free hydrogen ions.

It is therefore a primary objective of this invention to provide a substance which is permeable through the cell membrane in tissue cells or passes the blood-brain barrier and which also exerts a buffering action on the increase of the hydrogen ion concentration, which compound would be effective in protection of irreversible injury of said cells due to lactic acidosis caused by oxygen deficiency.

SUMMARY

One aspect of the present invention is a method for protection of tissues and cells in the mammalian body from the irreversible damages due to lactic acidosis caused by the accumulation of lactic acid in the tissues and cells under the condition of oxygen deficiency, which method comprises administering to a mammal a non-toxic substance for which the cell membrane is permeable, which is able to cross the blood-brain barrier and which is able to exert a buffering action in the cells and tissues against the increase of the hydrogen ion concentration.

Another aspect of this invention are compounds useful for protection of tissues and cells from the irreversible injury due to the over production of the free hydrogen ions, which compounds are permeable through the cell membrane and possess a buffering capability to prevent and neutralize an increase of hydrogen ion due to an insufficient supply or availability of oxygen.

Still another aspect of this invention are compounds which cross the blood-brain barrier, which are cell membrane permeable, which possess a buffering action against increase of the hydrogen ion, have preferably pH of no less than 6.8, which behave as hydrogen ion acceptor and which are chosen from the group of monocyclic heterocyclic compounds, polycyclic heterocyclic compounds and ring assembled heterocyclic compounds, all of these compounds having at least one nitrogen atom and preferably having at least one of the following functional groups: $-NH_2$, $>NH$, $\geqslant N$, $>N-OH$, $-NH-OH$, $=N-OH$, $>N-O-$, $-N-H-O-$, $-COONH_2$, $-CO-N<$, $-CO-NH-$, $-CO-NH_2$, $(-CO-)_2N$, $(-CO-)_2NH$, $(-CO-)_3N$, $C-N-$, $>C=NH$, $-C(NH_2)$ $(-C-)_n$ COOH, wherein n is 0–4, $-NH-C(NH)-NH_2$, $=C(NH)-NH_2$, $-NH-NH_2$, $=N-NH_2$, $-NH-NH-$, $-N=N-$, $-NH-CO-NH-$, and $-NH-CO-NH_2$.

Still another aspect of this invention is a method for protection of cells and tissues against anoxic injuries by providing a patient facing or encountering oxygen deficiency, the compound or the buffering system of the current invention having the buffering capability to encounter the metabolic acidosis caused by oxygen deficiency and/or prevent its development.

DETAILED DESCRIPTION OF THE INVENTION

Figure 1:
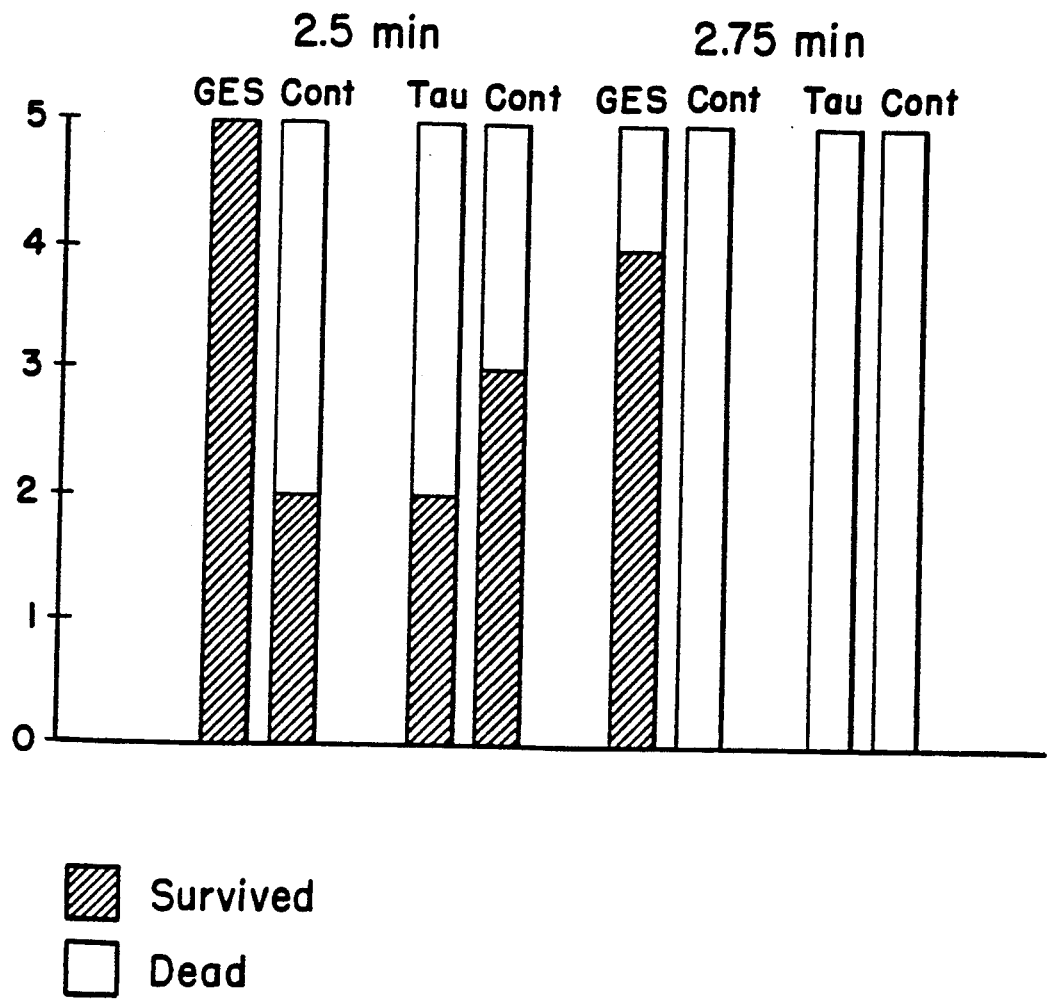
FIG. 1 illustrates the survival rate of adult mice exposed to anoxia pretreated with guanidinoethane sulfate or taurine compared to controls treated with saline.

This invention concerns and provides compounds and a method for protection of cells, particularly central nervous system cells, from the irreversible injury caused by the deficiency of oxygen or by the overproduction of hydrogen ions. Both these events cause the metabolic, particularly lactate acidosis, change in tissue and cell pH, and ultimately result in irreversible injury and/or death of cells.

Compounds of this invention are able to provide an additional buffering system which system effectively counters a metabolic acidosis, maintains a stable pH in tissues and cells and in this way protects tissue homeostasis.

The discovery of this invention is based on and is an extension of the primary homeostatic requirement for the constancy and the regulation of the internal bodily environment of which an indivisible part is a cellular stability and ions and ionic balance. Bodily internal ionic balance is maintained by buffer systems which efficiently accommodate the addition or formation of moderate amounts of acid or base without marked change in the hydrogen ion concentration.

In adults individuals, homeostasis or the equilibrium of the hydrogen ion concentration is maintained by the extremely sensitive buffering system comprising a combination of carbonate and non-carbonate buffer system. The combination buffer system contains carbonate, bicarbonate, phosphate, sulfate and protein buffers. The results of NMR measurement obtained and described below suggests, however, the presence of a third buffering system in newborn individuals. This system somehow neutralizes the hydrogen ion produced by the dissociation of the lactic acid accumulated under the condition of oxygen deficiency and allows maintenance of the constant pH in central nervous system cells around pH 7.24.

Such a system requires an equilibrium mixture of ions and undissociated molecules which will resist any attempt to disturb the intracellular pH and will be able to maintain it at physiological levels.

The cellular pH at 7.24 represents physiologically optimal conditions and pH 6.8 represents the absolute low limit to the physiologically acceptable conditions. When the pH level drops around or below this point, the survival of cells becomes extremely difficult.

The survival of cells depends not only on the low pH levels but also on the length of time the cells are submitted to such low pH levels. Thus, for example, a momentary drop of pH to 6.8 would probably not result in permanent injury to cells if it would be immediately neutralized by buffering action and pH would be brought to the physiologically acceptable levels. On the other hand, the extended time exposure to pH around 6.8–7.0 would probably result in irreparable injury to cells and tissues. It is therefore important that the effective buffering system is available to assert immediate buffering action at any time when pH drops under the 7.24 and particularly if it drops to levels around 6.8.

The most efficient buffering action of a compound is expected within a range of the pH value being nearly equal to its pKa value. Thus, the new buffering compound should have a pKa value of not less than 6.8, but preferably higher, or the buffering system containing such compound should be a combination of compounds of which the cumulative pKa is at least 6.8.

The new compound and/or new buffering system will have to work according to the principle of a buffer solution, illustrated as follows:

A weak acid (HA) in solution partially dissociates into proton and its conjugate base ($A^-$). Such a solution has the buffering capacity, i.e., the ability to resist pH changes when a base or acid is added to it. If a strong acid is added to the buffer solution, the hydrogen ions are picked up by the conjugate base of the buffer according to equation:

$$H_2O^+ + A^- \rightarrow HA + H_2O$$

If a strong base is added to the buffer solution, the hydroxyl ions are picked by the weak acid of the buffer, according to the equation:

$$OH^- + HA \rightarrow A^- + H_2O$$

The solution is most efficient as a buffer when it contains equal amounts of a weak acid (HA) and its conjugate base ($A^-$).

According to the Henderson-Hasselbalch equation, the pH of the buffering system depends on the compound's pKa and thus $$pH = pKa + \log(A^-/HA)$$

When HA equals A, $\log(A^-/HA)$ equals zero. Therefore, a buffer solution has optimal buffering capacity at pH=pKa.

The illustration of one buffer system which is present in the body and is connected with and responsible for the disposition of an excess of hydrogen ions formed during metabolic acidosis is a carbonate buffer. The carbonate buffer system represents the main buffer system for mammals. At physiological pH, i.e., at pH=7.4, carbonate ($CO_3^{2-}$) levels are negligible and, therefore, cytosolic carbonate is either in the form of carbonic acid ($H_2CO_3$) or bicarbonate ($HCO^-_3$). Titration studies have shown the pKa value of physiological carbonic acid/bicarbonate solution with $pCO_2$ of 40 mmHg at 37° C. to be 6.12.

$$H_2CO_3 \underset{pKa = 6.12}{\rightleftharpoons} HCO_3^-$$

Therefore, it is apparent that carbonate itself is not an optimal buffer at physiological pH.

Despite its less than optimal pKa value to buffer at physiological pH, the carbonate system has one critical advantage for biological systems, namely, a rapid adjustment of carbonic acid levels by manipulation of $pCO_2$. Metabolic acidosis brought about by excess acid formation is known to be quickly compensated by a decrease in $pCO_2$ by hyperventilation. This rapid control by respiration is a notably very efficient and accurate system for acid-base control. This mechanism is well-developed in normal healthy adult mammals but is not usable for fetus and is underdeveloped in newborn mammals. Thus, it is logical that both a fetus and newborns possess some other mechanism how to prevent tissue acidosis.

Attempts to measure and compare the lactate ion concentration and the hydrogen ion concentration in the central nervous system cells of newborn rats and mature rats placed under the condition of oxygen deficiency, using nuclear magnetic resonance (NMR) spectroscopy, revealed that there is no significant difference with regard to the increase of the lactate ion concentration between newborn rats and adult rats. Thus, the higher concentration of lactose were observed in both newborns and adult animals following the anoxic exposure. However, a significant difference was produced when the hydrogen ion concentration was measured. Namely, it was found that the hydrogen ion concentration in adult rats was increased in proportion to the increase of the lactate ion concentration, while the hydrogen ion concentration in newborn rats increased only slightly with the increase of the lactate ion concentration. Thus, there was dependence of the hydrogen/lactose ion concentration in adult animals while no such dependence was observed in newborn animals. This observation suggests the presence of some additional or different mechanism which prevents development of acidosis in newborns.

One of the most dramatic alterations in the mammal associated with birth is the change in lung function. During fetal life, $pO_2$ and $pCO_2$ homeostasis are totally dependent on the mother. Following birth, these come under the newborn's own control. While $O_2$ is an essential substrate for biological energy production in oxidative phosphorylation, $CO_2$ plays a fundamental role in acid-base balance as a part of the carbonic acid/bicarbonate buffer system. Hemoglobin, the blood oxygen delivery system, is present in the fetus in an unique type called fetal hemoglobin. Fetal hemoglobin undergoes dramatic adaptational changes after birth to the adult type normal hemoglobin. It would therefore not be surprising if the acid-base regulatory system would similarly possess a specific system during fetal life which undergoes adaptational changes to the adult type system after birth.

In view of the above findings that the newborn mammals possess a certain mechanism to prevent damage due to oxygen deficiency, the search for any substance present in newborn cerebral cells which may be present in extraordinary quantities in newborns or which is not present in adults, was initiated. Such substance would have to be present in neuronal cells during the fetal period in a considerable amount, should be able to cross the blood-brain barrier but should decrease rapidly after birth.

As the result of such research, it is now believed that an amino acid taurine is such a substance. Taurine seems to be present in high amounts in newborn animals but in much smaller amounts in adult animals. It does cross the blood-brain barrier in newborns but it has no such effect in the adults. It possesses excellent buffering properties. Therefore, conceivably, taurine could be a key substance forming said third buffer system present in fetus or in newborn mammals.

When quantitatively measured, it has been discovered that taurine is present in the cerebral cells of newborn rats immediately after birth in the relatively high levels of about 18 mM and is subsequently decreased to a low level of about 4 mM within about one month after birth. At that time, taurine is replaced by N-acetylaspartic acid (NAA) for the maintenance of the osmotic pressure and ionic balance in cerebral cells which was previously, before and early after birth, maintained by taurine containing buffer.

Taurine (2-aminethanesulfonic acid) of formula NH₂CH₂CH₂SO₃H is a primary amine containing compound having pKa value 8.74 which compound exhibits a buffering action against the increase of the hydrogen ion concentration under the physiological conditions. To the contrary, N-acetylaspartic acid is a dicarboxylic acid which does not show a buffering capacity with regard to the increase of the hydrogen ion concentration. Levels of taurine and NAA were studied with respect to their changes dependent on the time after birth of the animal.

Relative taurine and NAA levels were assessed using high resolution proton spectroscopy of brain perchloric acid (PCA) extracts. One and 10 days old pups were sacrificed immediately after completion of the study by exsanguination under pentobarbital anesthesia. Brains were removed and fixed in liquid nitrogen. The frozen brains were pulverized in a liquid nitrogen cooled mortar and pestle and mixed with powdered frozen PCA, 0.5N, 4 volumes. The powder mixture was centrifuged in liquid nitrogen cooled centrifuge tubes at 16,000 r/min at $-4°$ C. for 30 minutes.

Figure 6:
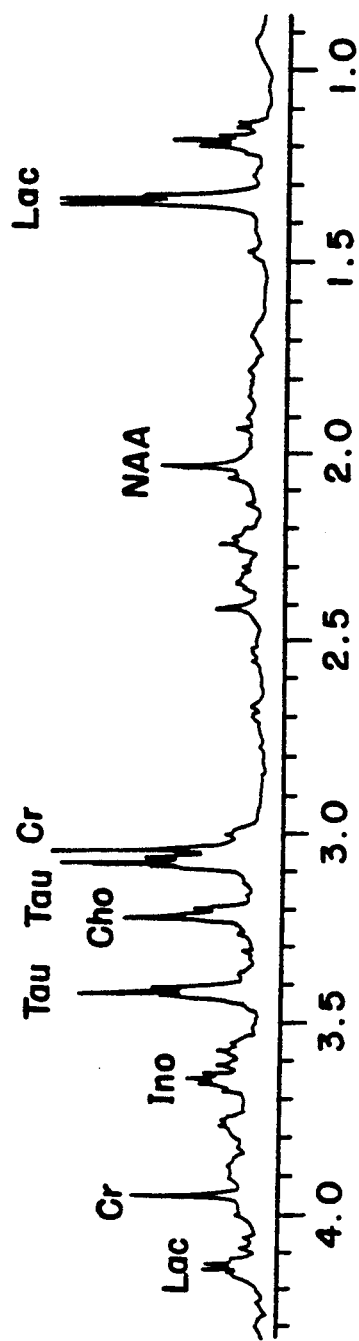
FIG. 6 is representative high resolution proton spectrum of PCA extract of pup brains.
Figure 7:
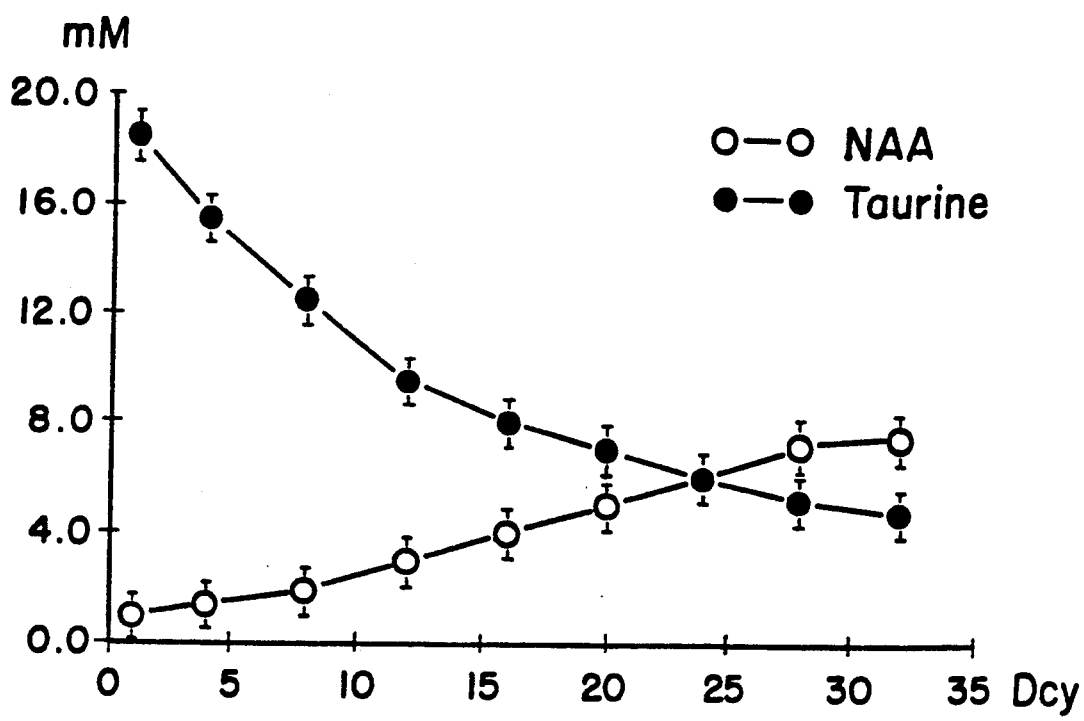
FIG. 7 show the developmental changes in taurine and n-acetylaspartic acid levels in newborn and adult (32 day old) mice.

FIG. 6 is a representative high resolution proton spectrum of pup brain PCA extract showing the presence of creatine, inositol, taurine, choline and NAA, wherein the concentration of NAA is much lower than that of taurine in 10 day old pups. FIG. 7 is a summary of the developmental changes in brain taurine and NAA levels which show an inverse replacement correlation. As seen from FIG. 7, immediately after birth the level of taurine is around 18 mM while the level of NAA is only around 1 mM. At day 10, the level of taurine is already substantially decreased to levels around 11 mM, while the level of NAA is only about 2.5 mM, but increases steadily on daily basis. On day 26, both levels of taurine and NAA reach the same level of around 6 mM. The level of taurine then declines to around 4 mM at day 32, at which day the level of NAA reaches approximately 8 mM.

Figure 8:
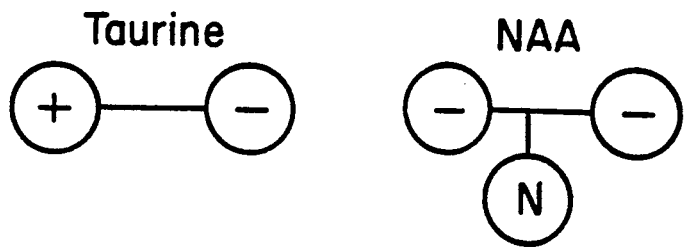
FIG. 8 illustrates a change in diffusion environment due to replacement of taurine with n-acetylaspartatic acid.

Replacement of taurine by NAA can thus far be summarized to accomplish two main effects on the intracellular environment: (1) changes in cytosolic buffer system from fetal, taurine containing type to adult, NAA containing, type; and (2) maintaining ionic balance after depletion of fetal taurine. In addition, replacement of taurine by NAA appears to have one more effect on the cytosol environment, namely, a change in the diffusion environment. At physiological pH, the main form of taurine is $NH_3^+$-R-$SO_4^-$ while most of NAA is in the form of -OOC-R-COO- as seen in FIG. 8.

Individual taurine molecules tend to attract, while NAA molecules tend to repel each other. It is conceivable, therefore, that passive diffusion of a negatively charged substrate such as ATP in cytosol may be faster in an NAA solution than in a taurine solution. ATP is a molecule which requires delivery from its production site (mitochondria) to the main consumption site (plasma membrane) by passive diffusion in the cytosol. Oxidative phosphorylation in mitochondria is much more active in adult brain than in fetal brain. ATP consumption at the Na-K pumps is also much more active in adult brain than in fetal brain. Therefore, faster ATP diffusion within the cytosol is desirable in mature brain. NAA replacement of taurine may indeed positively affect ATP diffusion in cytosol, however it definitely affects negatively the buffering capability.

Said phenomenon, i.e., the existence of taurine in newborn rats and its subsequent substitution with N-acetylaspartic acid indicates that the cerebral cells of newborn rats just after birth are provided with an additional buffering function to prevent the increase of the hydrogen ion concentration therein. However, such buffering function is rapidly lost with time. Its presence explains why newborn mammals show significant resistance to oxygen deficiency in comparison with adult animals or humans.

While the rapid control of acidosis is readily available to the normal and healthy adult mammal, including human being, and to a certain degree, even to a newborn baby, the fetus in utero cannot take advantage of this rapid adjustment system since the fetal $pCO_2$ is heavily dependent on factors, such as placental blood flow and maternal $pCO_2$, uncontrollable by the fetus itself. Therefore, it seems likely that the fetus has an alternative means of maintaining acid-base homeostasis.

Since taurine has been shown to be present in extremely high amounts in the brains of fetus and newborn mammals, the function of taurine as a buffering compound has been examined and the taurine-like buffer proposed in this invention which could be used to counter the acidotic changes in adults which, for any reason have their normal buffering system damaged or which cannot is sufficiently counter severe acid-base disbalance.

Taurine is ubiquitous in mammalian organs. Taurine levels are especially high in the brain of the fetus reaching 18 mmol/l in rat and rapidly declining after birth to adult levels of 4 mmol/l in adult rat. Although the nutritional aspects of taurine are often emphasized, the majority of taurine in the brain exists as the free amino acid in the cytosol and is thought to be metabolically inert. At physiological pH, virtually all taurine is in the form of R-$SO^-_3$ and can be considered to be a weak acid such as R-$NH_3$, with a pKa value of 8.74, as shown below.

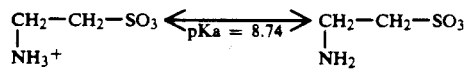

Based on the high levels of taurine in the fetus and in early life, on its presence in the cytosol, and on its buffering capability shown above, the current discovery proposes that the fetal taurine is a part of the cytosolic buffer and in the fetal brain it optimizes cytosolic buffering capacity at physiological pH and that in this way it would be also useful in compromised adults in the same way as in fetus or infants, if delivered in an appropriate form.

All alone taurine has a pKa=8.74 and by itself has doubtful physiological function. However, if combined with carbonate (pKa=6.12) it would conceivably provide a useful buffering system. In the process of this invention, taurine analogues and taurine-like compounds have therefore been used to prepare taurine/carbonate or taurine-like/carbonate buffers and such buffers were investigated for their possible role as the acid-base control. Using the standard pH of interest, two buffer solutions with different pKa values, i.e., taurine/carbonate and taurine-like/carbonate buffers were prepared, wherein compounds in the appropriate molar ratio were mixed.

Brain carbonate levels at physiological conditions are estimated to be 23 mmol/l in rats, while taurine levels in rat fetal brain were shown to be 18 mmol/l. Theoretically thus, a mixture of physiological carbonate buffer having pKa 6.12 and the physiological taurine buffer having pKa=8.74, in a molar ratio of 23 to 18, provides a buffer solution with a newly optimal pKa value of 7.27. Therefore, it appears that cytosol of fetal brain indeed has a buffering capacity optimal at physiological brain pH.

In the same manner, other taurine analogs, such as guanidinoethane sulfate, guanidinoethanesulfonic acid or taurine-like compounds having similar properties, such as pKa buffering capability, ability to act as the hydrogen ion acceptor, being membrane permeable or able to cross blood-brain barrier, are useful as active compounds in preparing buffers of this invention.

Figure 4:
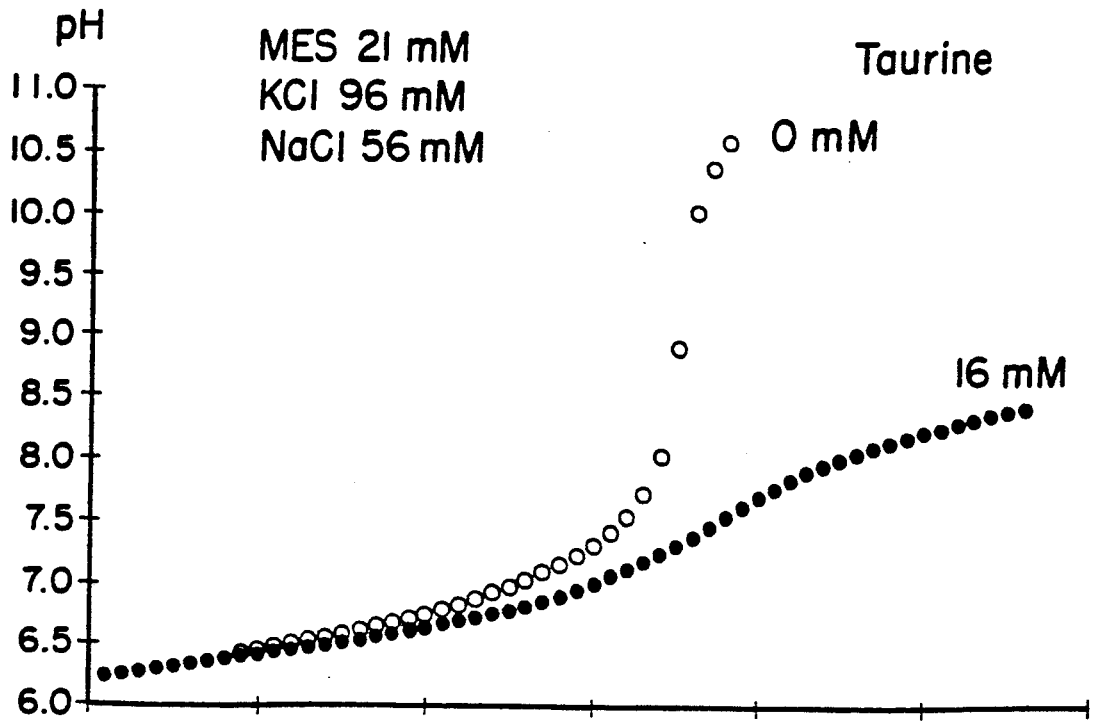
FIG. 4 illustrates the optimization of the 2-(N-Morpholino)ethanesulfonic acid buffer system containing taurine.
Figure 5:
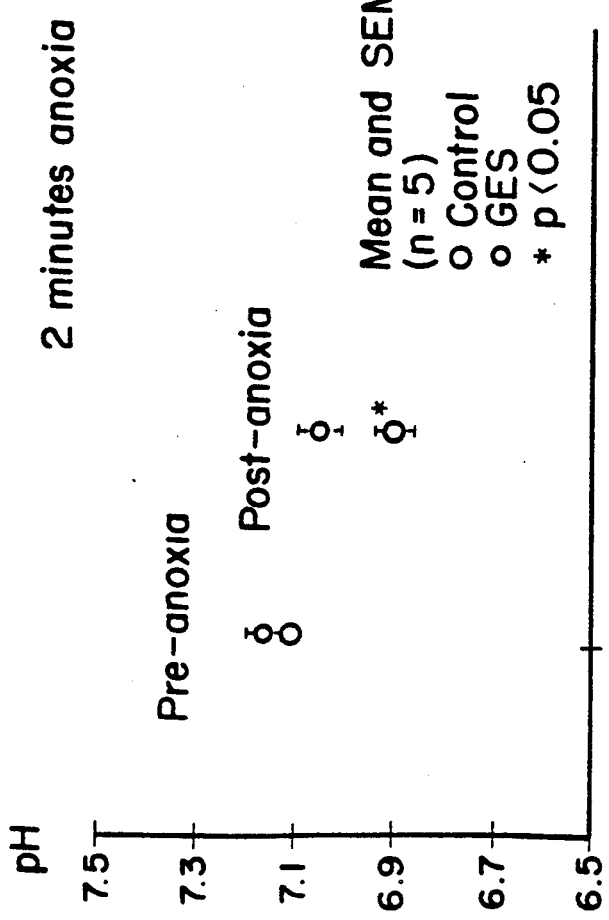
FIG. 5 illustrates the pH changes following the 2 minutes anoxia in the brain of control and GES pretreated adult mice.

This point was tested and is illustrated by FIG. 4, which shows that taurine can optimize buffer effect when added to 2-(N-Morpholino) ethane sulfonic acid (MES) buffer (pka 6.1) in the same physiological concentration as that of brain carbonate, to result in taurine/MES buffer of around pH 7.2. The MES buffer is used as the carbonate buffer equivalent for in vitro titration studies because it does not involve gaseous $CO_2$.

The pKa values of inorganic phosphate (Pi), adenosine diphosphate (ADP) and adenosine triphosphate (ATP) relevant to the maintenance of the physiological pH are 6.80, 6.88 and 6.95, respectively. The estimated normal levels of these components in the rat brain are 0.4 mmol/l for ADP and 3 mmol/l for ATP. Under normal conditions, the estimated potential contribution of Pi to the cytosol buffer is 0.6 mmol/l. If the contribution of ATP/ADP/Pi is taken into account, the cytosol buffer solution is optimal at pH 7.23, a very close pH to taurine/carbonate buffer of PH 7.27.

The substance useful as the active component of the buffering system in the method of this invention is required to be non-toxic, to be able to cross the blood-brain barrier and/or to possess a cell membrane permeability, and possess a buffering action for the hydrogen ion concentration.

Based on the above-stated criteria, the requirement for the compound useful in practice of this invention is as follows.

Said substance useful as an active component of the buffering system of the method of this invention may be any non-toxic substance, either endogenously present in the cells or synthetic, particularly any nitrogen-containing basic substance, which is permeable through the cell membrane in tissue cells, such as cerebral cells and/or must be able to pass the blood-brain barrier, and be able to exert a buffering action on the hydrogen ion concentration in those cells suffering from lactic acidosis under the condition of oxygen deficiency. The active compound has preferably a pKa of not less than 6.8.

In general, nitrogen-containing compounds behave as a weak basic substances, and their ionic type molecules and non-ionic type molecules coexist in physiological solutions. The ionic type molecules have difficulty to permeate through cell membranes (except when actively transported through the membrane in kidneys cells, for example), while the non-ionic type molecules are cell membrane permeable due to a diffusion mechanism restricted by a lipid barrier.

When the non-ionic type molecules which permeate through a cell membrane reach a concentration equilibrium on both sides of the cell membrane, the ratio of the concentration of a nitrogen-containing compound inside to outside of the cell membrane can be expressed by the following equation:

$$\frac{C_{in}}{C_{out}} = \frac{1 + 10^{pKa-pH\,(in)}}{1 + 10^{pKa-pH\,(out)}}$$

wherein $C_{in}$ and $C_{out}$ are, respectively, the concentrations of the nitrogen-containing compound at the inside and outside of the cell membrane, pKa is the pKa value of the nitrogen-containing compound, and pH(in) and pH(out) are respectively the pH value at the inside and outside of the cell membrane.

As understood from this equation, the concentration of the nitrogen-containing compound in cells is increased when its pKa value is higher than the pH value inside the cell. Thus, the use of a nitrogen-containing compound having a pKa value higher than that of blood plasma (i.e., 7.4) is desirable in order to favor entry of the compounds into cells to increase the concentration of said compounds available for buffering excess hydrogen ions.

The active substance behaves generally as a hydrogen ion acceptor and is expected to exert a buffering action against the increase of the hydrogen ion concentration. The active substance may be chosen from monocyclic heterocyclic compounds, condensed polycyclic heterocyclic compounds and ring assembled heterocyclic compounds, all of these compounds having at least one nitrogen-atom. Additionally, active compound may be chosen from nitrogen-containing compounds having at least one of the following functional groups —NH$_2$, >NH—, ≫N, >N—OH, —NH—OH, =N—OH, >N—O—, —NH—O—, —COONH$_2$, —CO—N<, C—N—, —CO—NH—, —CO—NH$_2$, (—CO—)$_2$N, (—CO—)$_2$NH, (—CO—)$_3$, >C=N—, >C—NH, —C(NH$_2$) (—C—)$_n$ COOH, wherein n is 0-4, —NH—C(NH)—NH$_2$, =C(NH)—NH$_2$, —NH—NH$_2$, =N—NH$_2$, —NH—NH—, —N=N—, —NH—CO—NH—, and —NH—CO—NH$_2$.

The exemplary compound of this invention is the taurine-like compound, and all taurine endogenous and synthetic analogs, such as guanidinoethane sulfate. Other compounds having the same or similar properties as taurine and possessing the required buffering capability which may be either inhibitors and/or competitors of taurine are equally contemplated to be within the scope of this invention.

To test the taurine buffering capability during anoxia, the taurine/carbonate buffer was tested in neonatal brains and the acid-base balance of neonatal brains in response to anoxia was evaluated by new approach using in vivo NMR spectroscopy. Research on brain acid-base equilibrium has been previously hampered by technical limitations. The development of nuclear magnetic resonance (NMR) in vivo spectroscopy has provided unprecedented opportunities in the research of acid-base balance of the brain. Now, intracellular pH and lactate measurements can be readily performed in live animals under various conditions using proton ($^1$H) and phosphorous ($^{31}$P) NMR spectroscopy.

A Nicolet NMR System NT-200 (4.7T) was used for NMR experiments. Mice, rats or pups (Sprague-Dawley) were lightly anesthetized with ketamine hydrochloride, 50 mg/kg I.P., and placed in the NMR probe which contained an oval surface coil (one turn, 8×12 mm diameter) tunable to the resonance frequency of the proton and $^{31}P$. To eliminate signal contamination, scalp and temporal muscle were retracted. Field homogeneity was maximized by shimming on water proton signals. To produce anoxia, 100% nitrogen gas was rapidly infused (14 l/min) into the probe chamber. Anoxia could be reversed by infusion of air. Calibration studies using an oxygen meter (OM-1 Biological oxygen Meter, Micro-electrodes, Inc.) confirmed that this technique produced complete $O_2$ depletion in the chamber or its reversal within 1 minute. $^1H$ spectra were obtained at 199.97 MHx=z using a $\overline{1331}$-$\tau$-$\overline{2662}$ spin echo sequence with a $\tau$ delay of 68 ms (spectral width: 2 kHz, memory block: 4K, recycle time 2.7 seconds). The interpulse delay of the Hore sequence was adjusted so that the lactate resonance experienced least attenuation. $^{31}P$ spectra were obtained at 80.99 MHz using a one pulse sequence (spectral width: 6 kHz, memory block: 4K, recycle time 2.7 seconds). The free induction decay (FID) like signals from remaining water proton signals were eliminated by applying sine function apodization. The broad resonance with short $T_2$ on $^{31}P$ NMR spectra was removed using the convolution difference technique. Line broadening of 5 Hz and 30 Hz were applied as noise filter for proton and $^{31}P$ spectra, respectively. Intracellular pH was calculated using the equation: $pH = 6.77 \log (\delta-3.29)/(5.68-\delta)$, where $\delta$ is the chemical shift of inorganic phosphate (Pi), referred to that of phosphocreatine (PCr) as obtained by this technique.

Figure 2:
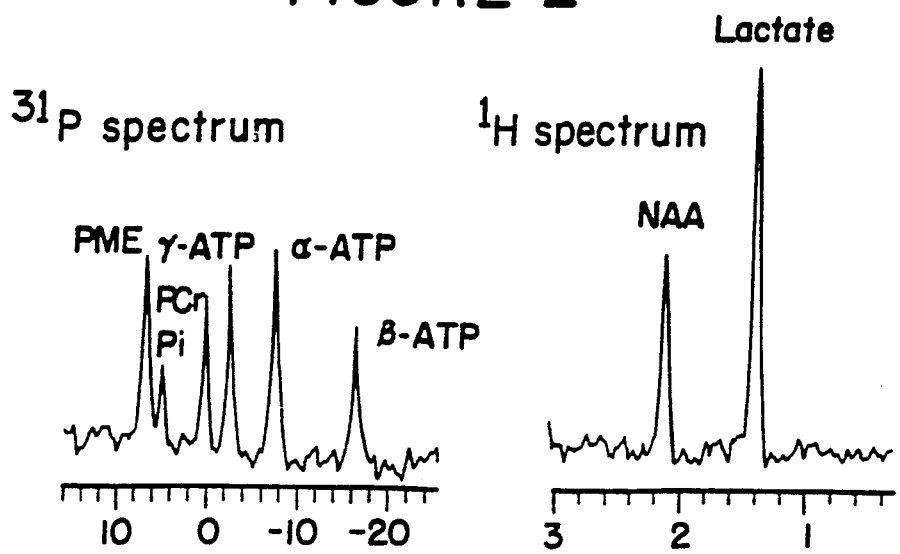
FIG. 2 represents $^{31}P$ spectrum of the brain of 10 day old rat pups following 7.5 minutes of anoxia.
Figure 3:
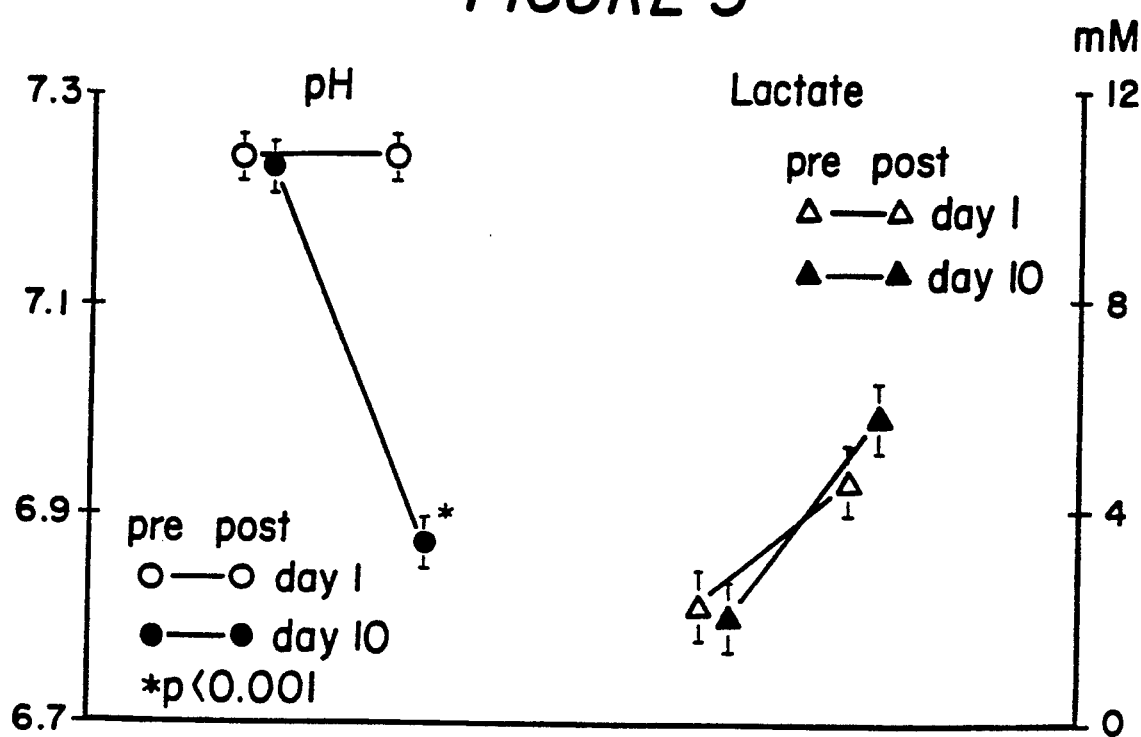
FIG. 3 shows changes in intracellular pH and lactate levels of 1 day and 10 day old pups following 7.5 minutes anoxia.

FIG. 2 shows representative proton and $^{31}P$ spectra of 10 day old pups following 7.5 minutes of anoxia. FIG. 3 summarizes the results obtained by measurement of intracellular pH and lactate levels in 1 day (n=10) and 10 day old pups (n=10) following 7.5 minutes of total anoxia. Brain taurine levels were 18 mmol and 11 mmol/l for day 1 and day 10 pups, respectively. The remarkable ability of 1 day old pup brain to preserve normal pH in spite of significant accumulation of lactate was observed.

When the comparison was made between the control group of newborn rats and the experimental group injected with taurine in the amount of 16 mmol/kg/day of taurine for 2–10 days and both groups were subjected to anoxia, according to Example 1, the pH in the brains of newborn rat pups pretreated with taurine was only slightly decreased following the anoxia to pH 7.0 from 7.3 before anoxia, while the brain of the control group dropped to pH 6.85, which pH would sooner or later lead to brain cells injury and death.

At the same time, the amount of lactic acid in both the experimental and control groups increased substantially from preanoxia level of 0.7, expressed by the lactic acid/N-acetyl aspartate, to 2.4 post anoxia. There was no difference observed between the experimental and control groups.

The above results indicate that anaerobic glycolysis due to anoxia proceeds in both the experimental group and in the control group and leads to accumulation of lactic acid to the same extent in both groups. To the contrary, the pH depression is considerably prevented in the experimental group by the buffering action of taurine administered as a pretreatment to the experimental group, while the pH drops to a dangerous limit in the control group which was not pretreated with taurine.

Similar results were observed and are illustrated in FIG. 3. One day and ten days old pups were submitted to 7.5 minutes of anoxia and their pH values and lactate levels before and after the exposure were determined.

As seen in FIG. 3, pH level in one day old pups did not change even after 7.5 minutes anoxia, while the pH in ten day old pups dropped to dangerous levels of 6.85. The lactate level was similar in both groups.

The depression of the intracellular pH caused by lactic acidosis in anoxia can thus be prevented by the buffering activity of an active compound, such as taurine, or other taurine-like compound which has a buffering activity at or below physiological pH. In other words, the resistance to anoxia is expected to increase when the active compound having the same behavior and properties as taurine is administered before the induction of anoxia.

One of the taurine-like compounds useful in the practice of the current invention is guanidoethanesulfonic acid or guanidinoethane sulfate. Guanidinoethanesulfonic acid is known to have ability to cross the blood-brain barrier (J. Pharmacol. Exp. Ther., 211: 465–471 (1980)). The pKa value of its amidine residue is 12.48. Guanidonoethane sulfate (GES), an analog of taurine has shown similar protective properties to taurine, when administered to adult mice prior to exposure to anoxia. Under the experimental conditions described in Example 3, after 2.5 minutes of anoxia, exposure, adult mice pretreated with GES had a zero mortality rate. Both control groups of adult mice pretreated with either taurine, which does not cross the blood-brain barrier in adult mice, or with physiological saline, and exposed to 2.5 minutes of anoxia experienced 40% mortality. When the anoxia period was extended to 2.75 minutes, the GES treated mice had 2 mortality rate of 20%, while the control groups' mortality rate, whether taurine or saline pretreated, reached 100%.

FIG. 1 illustrates the results showing the protective function of GES against fatal injury to the cells caused by drop in the pH. When compared to taurine and saline pretreated groups, as seen in columns 1–4, the pretreated group with GES provided 100% protection against 2.5 minutes long anoxia (column 1), while taurine, which does not cross the blood-brain barrier in adult (column 3), was only providing protection in 40%. 60% of the animals died in taurine and saline groups. Thus, there was no difference between taurine pretreated animals (column B) and saline pretreated animal (columns 2 and 4). Seemingly, the saline control group (column 4) did better than taurine group (column 3).

The results were even more pronounced when the anoxia exposure is extended to 2.75 minutes. While the mortality in GES pretreated group (column 5) was 20%, mortality in all other three groups, i.e., taurine and saline pretreated groups, 6–8 was 100% and there were no survivors.

These finding clearly show that the cell permeable, blood-brain barrier crossing compounds, which are taurine analogs are able to provide an excellent protection against the detrimental effects of oxygen deficiency and in this way protect the animal against irreparable injury due to the unphysiological increase in hydrogen ion concentration which would otherwise lead to cell death.

These results also show that for the short time anoxia exposure, the pretreatment of adult animals with GES is more effective than pretreatment with taurine or saline and can completely protect the animal from any detrimental effect caused by oxygen deficiency and prevent the injury of the cells due to lactic acidosis.

When the time of anoxia is extended to longer time, GES protects the adult animals to the extent that only 20% of all animals die while all taurine or saline treated animals die.

In the similar experiment, adult mice were used for determination of pH changes depending on pretreatment with GES prior to anoxia induced with nitrogen. The pH of the animals' brain in vivo was measured using NMR, before and after the nitrogen exposure. The average pH values in the brain before the anoxia were 7.16 for GES treated animals and 7.11 for saline treated animals. Thus, before anoxia, the difference was not significant. Following the exposure to pure nitrogen atmosphere, i.e., after anoxia period, the pH values in the GES treated animals were pH 7.05, while the pH value in the control, saline treated animals, was dangerously low at pH 6.90. Thus, the administration of GES significantly ($p<0.05$) prevented the decrease in the cellular pH in the animals' brains and prevented the brain injury in adult animals which normally do not possess the mechanism which would prevent such a pH drop.

While in adult animals taurine per se was not effective, because it does not cross the blood brain barrier, the protection by taurine pretreatment was seen in newborn or very young animals.

When the newborn 1 day old rat pups were tested against 10 day old pups and their levels of lactic acid and pH in the brain were determined in vivo using NMR spectroscopy, the one day old pups had an extraordinary ability to preserve normal pH even after 7.5 minutes anoxic exposure. As seen in FIG. 3, in 1 day old pups (          ) the pH prior and post anoxia was absolutely unchanged. To the contrary, for the 10 day old pups, (          )the post anoxia pH dropped sharply to levels under pH 6.9, which would cause irreparable injury to central nervous tissue.

In the same group, the level of taurine in the one day old pups was around 18 mmol/l while the level of taurine in 10 day old was around 11 mol/l.

When the levels of lactic acid were measured in the same two groups of 1 and 10 days old pups, as seen in FIG. 3, both groups experienced a similar increase in levels of lactate from around 2 mM to 5–6 mM. Thus the intracellular metabolism in both groups was very similar, but in 1 day old pups, the high level of taurine was able to preserve the normal physiological pH, while the 10 day old pups were subjected to a dangerous drop in pH due to tissue acidosis and to insufficient buffering capacity of available buffering systems.

This experiment clearly illustrates advantages of the current invention by providing an additional buffering system able to compensate for metabolic acidosis caused by insufficient supply of oxygen and metabolic over production of lactic acid and hydrogen ions.

UTILITY

The method and compounds of this invention may be used for protection of any tissue or cells from the irreversible damage and injury due to lactic acidosis and are particularly useful for treatment of acute cerebral ischemia, stroke, subarachnoid hemorrhage, vasospasm induced ischemia in tissue, brain trauma, spinal cord injury, chronic obstructive pulmonary disease, sudden infant death syndrome, drowning, accidental electrocution, CO and $CO_2$ poisoning during cardio-pulmonary resuscitation, in post operative brain, cardiac or vascular surgery as a component of cardioplegic solution for preservation of organs for transplantation, prevention of delayed neuronal death due to transient ischemia, in protection of fetus or prematurely born baby in management of risk group such as soldiers, miners or construction workers. Any disease or conditions which may result in ischemia or anoxic injury of the brain and other critical organs can be successfully prevented and/or treated with such agents.

The substances to be used as the active components in the method of this invention are different from the conventional drugs known and used up-to-date. The substances of this invention aim to suppress the increase of the hydrogen ion concentration in cerebral cells caused by lactic acidosis. They utilize their buffering action to reduce the action of the hydrogen ion in cerebral cells and in this way they prevent the cell damage injury or death.

The method of this invention can be used as the first aid in case of vasoconstriction or diminished of blood supply after cerebral infarction, ischemia, subarachnoid hemorrhage, cerebrospinal trauma etc., in both adults and newborns. In adults, the active compound will be such which will cross blood brain barrier, i.e., taurine-like compound or taurine analog. In newborns and infants, taurine and/or taurine-like compounds will be useful.

To a patient in need of such treatment, the compounds may be administered intravenously, orally, parenterally, through intravenous drip, or by intrathecal injection. In instances of diseases or injuries requiring blood oxygen supply, the treatment may be combined with or initiated by, for example, administration of thrombus removal agent such as streptokinase or by endarterectomy or angioplasty. However, even if oxygen blood supply is restored early, brain cells cannot endure over five minutes under anoxia. Therefore, the administration of the protecting agent of this invention alone or in conjunction with other drugs can be a life saving measure and the compounds of this invention will be able to ensure prolongation of cellular survival time to 20 to 30 minutes which will be sufficient to obtain the appropriate treatment.

The treatment using the compounds of this invention is also recommended as the protective step to assist the patients who are confronting a decrease in oxygen supply to brain caused by chronic pulmonary diseases with carbon dioxide retention, or following cardio-pulmonary operation. In the case where transient decreases or cessation of blood supply to brain is expected during operation of brain, heart or blood vessel, oral or parenteral administration of the protective agents of this invention for a designed period of time prior to the surgery will be effective in making brain cells resistant to anoxia during operation. In this way, accidental cell damage or death of brain cells due to delayed oxygen supply may be avoided.

The protective agents of this invention may be also useful for early treatment or prevention of injury of miners, construction workers or soldiers who may be accidentally exposed to hypoxia or anoxia, by administering agents of this invention regularly, for a certain period of time prior to the engagement of dangerous work, or post exposure.

The compounds of the current invention are similarly useful for protection of other than nervous tissue. Such other tissues as myocardium, for instance, may be irreversibly damaged when myocardial ischemia takes place and cardiac muscle cells become irreversibly damaged during ischemia due to lactic acidosis. In such an instance, however, the main aim is to avoid hyposystole of cardiac muscle brought upon by decrease of mycoplasmal troponin affinity to $Ca^{2+}$ during the period of pH lowering. The protective agents according to the invention are thus not only useful in prevention of myocardial ischemia as the target disease but are also effective to maintain the function of cardiac muscle until the proper therapy can be instituted. Specifically, for example in angina pectoris patients, regular oral administration of the lactic acid protective agent of this invention can assure protection of cardiac muscle. Further, for instance, in acute myocardial ischemia, administration of the agents of this invention orally, by coronary injection, or by intravenous drip in combination with percutaneous transluminal coronary angioplasty (PTCA) may be effective in protection of normal cells neighboring to effected myocardial cell.

Compounds of this invention may be formulated in any form acceptable in medicinal chemistry and pharmaceutical sciences.

The following Examples are intended to illustrate the invention. These examples are not be interpreted to limit the scope of the invention in any way.

EXAMPLE 1

Lactate Levels and pH in the Neuronal Cells

This example illustrates the measurement of pH and lactate concentration by NMR in rat pups.

Aqueous solution of taurine adjusted to pH 7 with sodium hydroxide in the amount of 16 mmole/kg/day was intraperitoneally administered to groups of Sprague-Dawley strain rats immediately after birth for 10 consecutive days. These animals were designated to be the experimental group. Physiological saline was administered to the control group of rats. Each group consisted of 10 animals.

On the last day of the administration, i.e. at day 10, the animals were each fixed in a special chamber set within a 4.7 T nuclear magnetic resonance apparatus. The normal atmosphere was replaced by pure nitrogen for 7.5 minutes. In this way, anoxia was induced in these animals.

The pH level and the lactate concentration in the cerebral cells before and after anoxia were measured by nuclear magnetic resonance spectroscopy using the procedure described above. Immediately thereafter, the brains were extracted, and the intracerebral taurine levels were quantitatively determined in the perchloric acid extraction fraction obtained from the extracted brains according to procedure described in Example 2.

The taurine amount (as expressed by the taurine/choline ratio) in the experimental group was $1.16+0.06$, and in the control group was $0.85+0.05$. There was a significant difference ($p<0.005$, t-test) observed between the two group. This experiment demonstrated that the administration of taurine to the newborn rats immediately after birth produces a significant elevation of the intracerebral taurine concentration.

The lactic acid amount, expressed by the lactic acid/N-acetyl aspartate ratio, was about 0.7 before anoxia and about 2.4 after anoxia, in both the experimental and the control groups. The increase of the lactic acid amount was caused by the production of glucose via anaerobic glycolysis in response to anoxia. The increase was not significantly different between experimental and control groups.

With respect to pH, a significant difference was observed between both groups. The pH value before anoxia was the same, of about pH 7.3, in both groups. In the experimental group, immediately after anoxia the pH dropped to pH 7.0 and to pH 6.85 in the control group. While the pH 7.0 is physiologically acceptable, pH 6.85 is borderline and would most probably result in irreversible damage to the brain cells, if not immediately treated.

EXAMPLE 2

In Vitro Taurine Assay

This example illustrates in vitro NMR method used for measurement and determination of taurine levels.

Taurine levels were determined in rat pups brains perchloric acid (PCA) extracts using high resolution proton spectroscopy. Pups were sacrificed immediately after completion of the study described in Example 1 by exsanguination under pentobarbital anesthesia. Brains were removed and fixed in liquid nitrogen. The frozen brains were pulverized in a liquid nitrogen cooled mortar and pestle and mixed with 4 volumes of 0.5N powdered frozen PCA. The powder mixture was centrifuged in liquid nitrogen cooled centrifuge at 16,000 rpm at $-4°$ C. for 30 minutes. The supernatant was removed and titrated to a pH of 9.0–9.5 by the addition of potassium bicarbonate. The solution was stored in an ice bath for 15 minutes and the potassium perchlorate precipitate was removed by centrifugation at 16,000 rpm at $-4°$ C. The sample was then lyophilized.

A Nicolet NMR System NM-500 (11.75T) was used for high resolution proton spectroscopy. Brain extracts were dissolved in 1 ml of heavy water and placed in a 5 mm NMR tube. Proton spectra were obtained using a one pulse sequence (recycle time 5.7 sec., flip angle 60°) with a spectral width of 6k into 16k memory blocks. The Lorentzian corrected height of the center resonance of the C-2 taurine triplet (3.43 ppm referred to trimethylsilyl propionic acid) and choline was used to obtain relative taurine levels. *Magn. Reson. Med.*, 12:172 (1989).

EXAMPLE 3

Guanidinoethane Sulfate Enhances Survival Rate of Mice Exposed to Anoxia

This example illustrates the protective effect of guanidinoethane sulfate against anoxia in adult mice.

GES was prepared according to method described in *J. Pharm. Exp. Ther.*, 211:466 (1979). Taurine and methyl isothiopseudourea were purchased from Sigma, St. Louis, Mo.

Sixty g of taurine were mixed with 100 g of methyl isothiopseudourea in concentrated ammonium hydroxide (120 ml) under a chemical hood. The mixture was heated to 60° C. and maintained at this temperature until evolution of gas ceased. The solution was cooled on ice until crystals were formed. Following the filtration, the crystals were dissolved in a minimum of distilled water and were recrystallized three times from water. Purity of GES was confirmed by proton NMR spectroscopy at 500 MHz (GE Omega-500). The pKa value of the amino moiety of GES was determined to be 12.48.

Adult Swiss mice (BK-1 males, 20 g) purchased from Bantin & Kingman, Fremont, Calif. were used. Each batch consisted of 10 mice. Within each batch five mice were selected randomly as experimental animals and the remaining five as controls. Experimental mice received daily intraperitoneal injections of 0.25 ml of GES (50 mg/ml) for 14 days. Control mice received either taurine (50 mg/ml) or sham injections of 0.25 ml of normal saline for 14 days.

At day 14, all mice within the same batch (5 experimental and 5 each of the two control groups) were placed in a specially designed chamber (26.5×24.5×21.0 cm). Anoxia/hypoxia was produced by infusion of pure nitrogen gas (14 ml/min) into the chamber for 2.5 or 2.75 minutes. Anoxia/hypoxia was reversed immediately after these intervals by removing the chamber and placing the mice in a room air environment.

Under this experimental setting, the $LD_{50}$ of anoxia/hypoxia duration is 2.5 min while 2.75 minutes is universally fatal for normal adult mice. Accordingly, two experimental settings, 2.5 and 2.75 minutes of anoxia/hypoxia duration, were chosen to determine the survival rate of GES, taurine and saline treated animals. The results are shown in FIG. 1 and discussed in detail above. Shortly, after 2.75 minutes of exposure, the experimental GES group showed a mortality of only 20%, while both control groups reached a mortality of 100%.

From the above results it is evident that sodium guanidinoethane sulfate can effectively prevent lactic acidosis caused by complete oxygen deficiency.

EXAMPLE 4

Effect of Guanidinoethane Sulfate Against in Vivo Intracellular Acidosis

Using the same experimental procedure as in Example 3, in vivo pH buffering property of guanidinoethanesulfonic acid against the in vivo intracellular acidosis and pH depression caused by anoxia was evaluated.

Aqueous solution of guanidinoethanesulfonic acid (0.3M) was administered daily intraperitoneally to five mice at a dose of 3.75 mmole/kg/day for a period of 14 days. The same number of control mice (5) received intraperitoneal administration of physiological saline solution at a dose of 0.25 ml/animal/day for the same period (14 days).

After the 14 days of administration period of GES or saline, animals were placed in a chamber filled with pure 100% nitrogen for 2 minutes to produce the anoxia state. The pH of the brain was measured in vivo before and after the anoxia by the technique of $^{31}P$ spectroscopy using Omega-7 Tesla Magnetic Resonance Spectrophotometer.

The average brain pH values before the anoxia were 7.16±0.04 and 7.11±0.01 for the guanidinoethane sulfate treated animals and for control animals, respectively. No significant difference in pH was observed between these two animal groups before the anoxia. On the other hand, the brain pH values after the anoxia were 7.05±0.05 and 6.90±0.04, for the guanidinoethane sulfate treated animals and for control animals, respectively.

Above findings clearly indicate that guanidinoethane sulfate effectively protects the brain cell from the acidosis damage, and against pH depression under the condition of anoxia, and in this way prevent the brain cells damage caused by lactic acidosis.

EXAMPLE 5

Effect of Taurine on Levels of Lactate, pH and on Brain Resistance to Fasting This example illustrates the effect of taurine on the levels of lactate, on the tissue pH and on brain resistance to acidosis following fasting.

Sprague-Dawley female rats 14-20 weeks old were mated to stud rats. Insemination was confirmed by the presence of sperm on vaginal smear to determine the due date and to ascertain age at delivery. Pregnant rats were fed laboratory chow ad libitum and allowed free access to water. Pups were born naturally. Individual litters contained 10-15 pups. Smaller litters were excluded.

An equal number of pups from the same dam were divided into three groups: control groups, taurine group, and fasting group. Each group contained 10 pups. Taurine pups received intraperitoneal injection of taurine (Sigma, St. Louis), 2 mg/g (water solution neutralized to pH 7 with a NaOH), daily, starting day 2 postnatally. The control fasting pups received sham injections according to the same protocol. Fasting pups were removed from the dam 48 hours prior to the experiments and were kept in a separate cage where their body temperature was kept normal by warming blanket. Pups were studied on day 10 postnatally.

A Nicolet NMR System NT-200 (4.7T) was used. Each pup was anesthetized with ketamine, 50 mg/kg. Pups were held in a specially designed padded holder which was placed in the probe chamber which contained a one turnaround surface coil (10 mm diameter) tunable to the resonance frequency of proton and $^{31}P$. The pup holder was positioned such that the surface coil was centered over the pup calvarium. To avoid signal contamination, scalp and temporal muscle were retracted. To produce anoxia, 100% nitrogen gas rapidly infused in amount of 14 l/min into the chamber. Anoxia was reversible by infusion of air. Calibration studies using an oxygen meter (OM-1 Biological Oxygen Meter, Microelectrodes, Inc.) confirmed that this technique produced complete $O_2$ depletion in the chamber or its reversal within one minute. The temperature of the chamber was kept at 32-33° C. by warmed air throughout the studies and monitored with a flexible nonmagnetic thermometer (YSI Series 402, Yellow Spring Instrument Co.). Field homogeneity was maximized by skimming on tissue water proton signals. $^{31}P$ spectra were obtained using a one pulse sequence at 80.99 MHz with a spectral width of 6K into 4K memory blocks (recycle time 2.7 sec.).

Previous studies under identical experimental settings indicated that contribution by substrates other than lactate to the resonance at 1.32 ppm is negligible in anoxia experiments on rat pups in the early postnatal stage. This is probably due to the lack of fatty acid release in response to anoxia in the early neonate brain.

For confirmation, calibration studies were performed on nine animals (three in each group) using a lactate editing method as follows. Proton signals were obtained during a two acquisition mode in a single sequence where the first acquisition is for a $\overline{1331}$-τ-$\overline{2662}$ and the second for $\overline{1331}$-τ-hard 180° pulse. Signals were stored in alternate mode into two different memory blocks (4k each). Total recycle time as 2.7 seconds with identical predelay time for each half. The interpulse delay of the Hore sequence was adjusted such that the lactate resonance observed least attenuation. 90 free induction decays (FIDs) were accumulated for each memory block. Signals stored in each memory block were processed separately, yielding proton spectra with a lactate resonance with and without 180° phase modulation acquired essentially at identical times. An edited lactate spectrum was obtained by subtracting the two spectra. The calibration studies confirmed that no substrate other than lactate contributed to the intensity of the resonance detected at 1.32 ppm significantly under these experimental settings in the 10 day old neonate. Accordingly, proton spectra for this study were obtained using a 1331-$\tau$-2662 pulse with a $\tau$ delay of 68 ms (spectral width: 2 KHz, memory block: 4k, recycle time 2.7 seconds).

The sum of 180 FIDs was blocked (7.5 minutes). Each animal was subjected to 7.5 minutes of total anoxia. $^{31}$P and proton spectra were obtained every 7.5 minutes starting 15 minutes before the anoxic period and for 45 minutes thereafter (total of 10 blocks). The broad resonance with short $T_2$ was removed using the convolution difference technique. The FID-like signals from the remaining water proton signals were eliminated by applying nine function anodization. Line broadening of 35 Hz or 5 Hz was applied as noise filter for $^{31}$P or proton spectra, respectively. Lorentzian corrected heights were used for quantification. For $^{31}$P data, the relative levels of each substrate were expressed as the ratio of the levels of each substrate to total phosphorus levels. Relative lactate levels were expressed as the ratio of lactate levels to N-acetyl-aspartate (NAA). Intracellular pH was estimated using the equation: pH-6.77+log ($\delta$-3.29)/(5.68-$\delta$), where $\delta$ is the chemical shift of Pi referred to that of phosphocreatine chemical shift of Pi referred to that of phosphocreatine (PCr).

Blood glucose levels after a period of 7.5 minutes of anoxia were determined using Chemstrip bG (Boehringer-Mannheim).

What is claimed is:

1. A method for protection of tissue cells from irreversible damages due to lactic acidosis caused by oxygen deficiency which method comprises administration to a patient in need of such treatment of a compound permeable through a cell membrane, or crossing the blood-brain barrier, which compound is able to buffer an increase in hydrogen ion concentration in the cells to the physiologically acceptable levels, wherein said compound is $NH_2CH_2CH_2SO_3H$, $NH_2-C(NH)NH(CH_2)_2SO_3H$, or $NH_2-C(NH)NH(CH_2)_2SO_3Na$.

2. The method of claim 1, wherein the cells are central nervous system cells.

3. The method of claim 2 wherein the compound is $NH_2CH_2CH_2SO_3H$.

4. The method of claim 2 wherein the compound is $NH_2-C(NH)NH(CH_2)_2SO_3H$.

5. The method of claim 4, wherein the patient is an adult.

6. The method of claim 4 wherein the patient is a newborn or infant.

7. The method of claim 3, wherein the patient is an adult.

8. The method of claim 3, wherein the patient is a newborn or infant.

* * * * *